United States Patent [19]

Nixon et al.

[11] Patent Number: 5,411,940
[45] Date of Patent: May 2, 1995

[54] USE OF TGF-$\beta_3$ TO REDUCE THE FORMATION OF SCAR TISSUE IN RESPONSE TO CORNEAL TRAUMA

[75] Inventors: Jon C. Nixon; Billie M. York, both of Fort Worth, Tex.

[73] Assignee: Alcon Laboratories, Inc., Fort Worth, Tex.

[21] Appl. No.: 128,460

[22] Filed: Sep. 29, 1993

[51] Int. Cl.$^6$ .................... A61K 37/02; A61K 37/36
[52] U.S. Cl. ......................................... 514/12; 514/21
[58] Field of Search ...................................... 514/12, 21

[56] References Cited

U.S. PATENT DOCUMENTS

| | | | |
|---|---|---|---|
| 4,717,717 | 1/1988 | Finkenaur | 514/21 |
| 4,962,091 | 10/1990 | Eppstein et al. | 514/2 |
| 4,981,841 | 1/1991 | Gibson | 514/2 |
| 4,983,580 | 1/1991 | Gibson | 514/2 |
| 5,057,494 | 10/1991 | Sheffield | 514/12 |
| 5,061,786 | 10/1991 | Burnier et al. | 530/326 |
| 5,108,989 | 4/1992 | Amento et al. | 514/12 |
| 5,124,392 | 6/1992 | Robertson et al. | 524/427 |

OTHER PUBLICATIONS

Derynck, et al. *EBMO Journal*, vol. 7, No. 12, pp. 3737–3743 (1988).
Schultz, G., et al., "Effects of Growth Factors on Corneal Wound Healing", *ACTA Ophthalmologica*, vol. 70, pp. 60–66 (1992).
ten Dijke, et al., *Proc. Natl. Acad. Sci. USA.*, vol. 85, pp. 4715–4719 (1988).
Connor, Jr., T. B., et al., "Correlation of Fibrosis and Transforming Growth Factor—$\beta$ Type 2 Levels in the Eyes", *The American Society for Clinical Investigations, Inc.*, vol. 83, pp. 1661–1666 (May 1989).
Khodadoust, A. A., "Pharmacology of Corneal Surgery", *Surgerical Pharmacology of the Eye*, edited by M. Sears and Tarkkanen, pp. 439–444, Raven Press, New York (1985).
Levine, et al., *American Journal Pathol.*, vol. 143, pp. 368–380 (1993).
Smiddy, W., et al., "Transforming Growth Factor Beta", *Archives of Ophthalmology*, vol. 107, No. 1, pp. 577–580 (1989).
Glaser, B., et al., "Transforming Growth Factor–$\beta_2$ for the Treatment of Full-thickness Mascular Holes", *Ophthalmology*, vol. 99, No. 7, pp. 1162–1173 (1992).
Glaser, B., et al., "Induction of a 'Retinal Patch' by Transforming Growth Factor-Beta in the Treatment of Full Thickness Mascular Holes", *Investigative Ophthalmology & Visual Science*, vol. 32, No. 4, p. 713 (Mar. 1991).
S. J. Ryan Chief Editor, "Retina", Chapter 68, published 1989 by the C. V. Mosby Company (St. Louis), pp. 229–242.
Cheifetz et al., Journal of Biol. Chem., vol. 265, No. 33, Nov. 25, pp. 20533–20536 (1990).

*Primary Examiner*—Howard E. Schain
*Assistant Examiner*—P. Lynn Touzeau
*Attorney, Agent, or Firm*—James A. Arno; Gregg C. Brown

[57] ABSTRACT

The use of TGF-$\beta_3$ to reduce the formation of scar tissue as a result of trauma to the cornea of the eye is described. The invention is particularly directed to the use of TGF-$\beta_3$ to reduce the formation of scar tissue in connection with ophthalmic surgical procedures involving the cornea, such as laser irradiation of the cornea. A composition containing TGF-$\beta_3$ is applied to the site of the trauma to alter the production and composition of extracellular matrix synthesized by fibroblasts, and thereby reduce the formation of scar tissue and consequent impairment of vision.

7 Claims, No Drawings

USE OF TGF-$\beta_3$ TO REDUCE THE FORMATION OF SCAR TISSUE IN RESPONSE TO CORNEAL TRAUMA

BACKGROUND OF THE INVENTION

The present invention relates to the field of ophthalmology. More specifically, the invention relates to a new method of promoting the healing of ophthalmic wounds, particularly corneal wounds.

The cornea is unique relative to other tissues. This is particularly true with respect to wound healing. The avascularity and transparency of the cornea represent two of its unique features. The avascular nature of the cornea generally causes a slower wound healing process, relative to vascular tissues. Moreover, maintaining the transparency of the cornea is vital to normal vision. The formation of scar tissue as a part of the corneal wound healing process can alter the transparency of the cornea, and thereby impair normal visual function. Controlling or modifying the corneal wound healing process therefore presents challenges which are both unique and of critical importance to the patient. The following text may be consulted for further details concerning the unique anatomical and physiological features of the cornea in relation to corneal wound healing: Khodadoust, A., "Pharmacology of Corneal Surgery," edited by M. Sears, et al., *Surgical Pharmacology of the Eye*, pages 439–444, Raven Press, New York, N.Y. (1985).

Relatively little is known about corneal wound healing, and yet new surgical procedures are being used and developed whose successful results depend entirely on how the wound heals. In some cases, the surgeon may wish to stimulate healing, such as in the promoting of re-epithelization following epikeratoplasty. However, in other circumstances, the surgeon may wish to retard healing, for example in cases of undercorrected radial keratotomy. Acceleration of the healing response through the use of certain growth factors and/or cytokines has been proposed previously. The following article may be referred to for further background information concerning the possible use of transforming growth factor-beta ("TGF-$\beta$") and other growth factors to treat corneal wounds: Schultz, G., et at., "Effects of Growth Factors on Corneal Wound Healing," *ACTA Ophthalmologica*, Vol. 70, pages 60–66 (1992). The use of TGF-$\beta$ to prevent corneal scar formation associated with laser irradiation of the cornea is described in U.S. Pat. No. 5,124,392 (Robertson, et al.; Alcon Laboratories, Inc.).

Three mammalian TGF-$\beta$ isoforms (denoted as $\beta_1$, $\beta_2$, and $\beta_3$, respectively,) have been identified. Each has a different specific gene loci. While the primary amino acid structure of these isoforms is highly conserved, there are clear differences in both the mature bioactive region and in the latency-associated peptide, both of which may confer biological specificity. See Akhurst, et al., *Mol. Reproduc. Dev.*, volume 32, pages 127–135 (1992). These isoforms have been found to share many of their biological activities at the cellular level. See Graycar, et al., *Mol. Endocrinol.*, volume 3, pages 1977–1986 (1989). However, it is being discovered that the isoforms may have quite different in vivo functions.

In studies on fetal wounds, it has been noted that healing occurs rapidly without the scarring associated with the healing of adult wounds. Fetal wounds are thought to have relatively high levels of TGF-$\beta_3$. TGF-$\beta_1$ and basic fibroblast growth factor are present in neonatal and adult wounds, but are not detected in fetal wounds. See Whitby, et al., *Devl. Biol.*, volume 147, pages 207–215 (1991). If fetal wounds are injected with TGF-$\beta_1$, scarring will occur, and if a specific antibody to TGF-$\beta_1$ is added to the wound, neutralizing the effects of the growth factor, scarring will be prevented. See Shah, et at., *Lancet*, volume 339, pages 213–214 (1992).

TGF-$\beta_1$ regulates extracellular matrix synthesis by a variety of mechanisms. See Amento, et al., *Ciba Foundation Symposium*, volume 157, pages 115–129 (1991). It stimulates the synthesis and secretion of extracellular matrix proteins, including collagen and fibronectin. In addition, it increases the expression of integrins and other membrane receptors which may facilitate cell migration into the wound. TGF-$\beta_1$ has also been shown to decrease the synthesis of proteases that degrade extracellular matrix, and stimulates the synthesis of endogenous protease inhibitors. All of these responses have been measured in fibroblasts; however, it is important to note that all fibroblasts do not respond in the same way to TGF-$\beta_1$. For example, collagen synthesis in fibroblasts isolated from the colon is suppressed by TGF-$\beta_1$. See Martens, et al., *Gut*, volume 33, pages 1664–1670 (1992).

In normal wound repair in an adult, marked differences are noted in the temporal and spacial relationships of the $\beta_1$, $\beta_2$, and $\beta_3$ isoforms of TGF-$\beta$ throughout the repair process. TGF-$\beta_2$ and TGF-$\beta_3$ are prevalent at 24 hours after excisional wounding and are associated with the migrating epidermis. In contrast, TGF-$\beta_1$ is not associated with any undifferentiated cells and is not present in the dermis and most dermal structures until five days after wounding, when re-epithelialization is completed. Following re-epithelialization, TGF-$\beta_2$ and TGF-$\beta_3$ are present in all four layers of the stratum corneum of the differentiating epidermis. This strongly suggests a role for TGF-$\ominus_3$ in dermal-epidermal interactions during wound repair. See Levine, et al., *Am. J. Pathol.*, volume 143, pages 368–380 (1993).

In view of the foregoing, it is clear that there are distinct differences between the in vivo activities of the $\beta_1$, $\beta_2$, and $\beta_3$ isoforms of TGF-$\beta$. This is particularly true with respect to TGF-$\beta_3$. The present invention is based on a new application of the unique properties of TGF-$\beta_3$. More specifically, the present invention utilizes the properties of TGF-$\beta_3$ to alter the healing of corneal wounds, so as to prevent scar formation.

SUMMARY OF THE INVENTION

The present invention is directed to the provision of an improved method of preventing or retarding the formation of corneal scar tissue associated with trauma to the cornea, including trauma associated with invasive and noninvasive corneal surgery. The invention is particularly directed to preventing or retarding the formation of scar tissue in connection with laser keratoplasty procedures, wherein an ultraviolet laser or other type of laser is utilized to alter the curvature of the cornea.

The improved method of the present invention utilizes a specific growth factor, transforming growth factor-beta-3 ("TGF-$\beta_3$"), as a mediator of the normal wound healing process. The properties of TGF-$\beta_3$ are unique relative to the other known isoforms of TGF-$\beta$. For example, TGF-$\beta_1$ is known to up-regulate (i.e., stimulate) the secretion of extracellular matrix components by fibroblasts. In contrast, the specific response of stromal fibroblasts to TGF-$\beta_3$ is believed to be a suppression of the inflammatory response, which may result in a relatively low production of extracellular matrix components.

While applicants do not wish to be bound by any theory, it is believed that TGF-$\beta_3$ prevents or retards the formation of scar tissue at the site of the corneal trauma by altering the production and composition of extracellular matrix components. This alteration of the extracellular matrix components, particularly fibronectin, collagen and glycosaminoglycans, greatly reduces scarring normally associated with these components during wound healing. TGF-$\beta_3$ is also believed to accelerate resurfacing of the corneal epithelium following trauma to the cornea by stimulating stromal cells to release factors which stimulate the growth and movement of corneal epithelium cells.

DESCRIPTION OF PREFERRED EMBODIMENTS

TGF-$\beta_3$ is one of five known isoforms of transforming growth factor-beta ("TGF-$\beta$"). The composition and properties of this polypeptide have been previously described in scientific and patent literature. See, for example, U.S. Pat. No. 5,108,989 (Amento, et al.; Genentech, Inc.), and the publications cited therein, particularly the following two scientific articles:

1) Derynck, et al., *EMBO J.*, Vol. 7, pages 3737–3743 (1988); and
2) ten Dijke, et at., *Proc. Natl. Acad. Sci. U.S.A.*, vol. 85, page 4715 (1988). The entire contents of the above-cited publications relating to the properties of TGF-$\beta_3$ and procedures for isolating and producing this polypeptide are hereby incorporated in the present specification by reference. The TGF-$\beta_3$ utilized in the present invention is preferably human derived. As used herein, the term "human derived" encompasses TGF-$\beta_3$ recovered from human tissues and TGF-$\beta_3$ produced from human cell lines by means of recombinant DNA technology.

The compositions utilized in the present invention contain TGF-$\beta_3$ in an amount sufficient to alter the normal formation of extracellular matrix components by fibroblasts at the site of the corneal trauma. As utilized herein, the term "extracellular matrix components" includes fibronectin, collagen and glycosaminoglycans. The amount of TGF-$\beta_3$ required for this purpose will generally be from about 0.001 to about 10,000 nanograms per milliliter ("ng/ml").

TGF-$\beta_3$ can be included in various types of pharmaceutical vehicles suitable for topical ophthalmic use. The vehicles are preferably aqueous, and are formulated so as to be chemically and physically compatible with ophthalmic tissues. For example, TGF-$\beta_3$ may be included in aqueous irrigating solutions, bioerodible gels or collagen inserts. The use of such gels or inserts has the advantage of providing sustained release of TGF-$\beta_3$ at the site of the trauma. However, the use of an aqueous solution as the vehicle for TGF-$\beta_3$ may be preferred in some cases. The aqueous solutions which might be utilized must be compatible with intraocular tissues, and should preferably help to maintain the integrity and function of intraocular tissues during the surgical procedure. The aqueous solutions which might be utilized for the above-described purposes include balanced saline solutions, such as BSS® Balanced Salt Solution and BSS Plus® Balanced Salt Solution Enriched with Bicarbonate, Dextrose and Glutathione, both of which are available from Alcon Surgical, Inc., Fort Worth, Tex., and BionTears TM, which is available from Alcon Laboratories, Inc., Fort Worth, Tex.

As will be appreciated by those skilled in the art, the above-described compositions must be sterile and should not include any agents (e.g., antimicrobial preservatives) which will be toxic to sensitive intraocular tissues, particularly corneal epithelial cells. The above-described compositions can be formulated in accordance with techniques known to those skilled in the art. The following publications may be consulted for further details concerning the formulation of compositions containing polypeptides, such as TGF-$\beta_3$: U.S. Pat. No. 4,717,717 (Finkenaur; Ethicon, Inc.); U.S. Pat. No. 4,962,091 (Eppstein, et al.; Syntex (U.S.A.) Inc.); and WO 92/15614 (Takruri; Chiron Ophthalmics, Inc.); and references cited in the foregoing patent publications.

The above-described compositions can be applied to the site of the trauma by means of various techniques. For example, the above-described solutions can be applied by irrigating the cornea with the solutions, and all of the above-described compositions can be applied by placing a small amount of the compositions in the cul de sac of the eye. The only critical requirement with respect to how the compositions are applied is that the compositions be distributed throughout the site of the trauma, and remain there for a length of time sufficient to alter the normal formation of extracellular matrix components by fibroblasts within the wound, in order to prevent or retard the formation of scar tissue. The amount of time required to achieve this purpose will vary somewhat depending on circumstances such as the particular type of trauma involved. However, the compositions will generally need to remain in contact with the site of the trauma for approximately five to thirty minutes or longer. The compositions should be applied immediately after wounding to suppress the cascade of other normal growth factor responses. A single application of the compositions will normally be sufficient. Multiple applications are generally not recommended, since this may initiate an inflammatory response. However in some cases, particularly diabetic patients, the need for multiple applications may override this concern.

As mentioned above, the present invention is particularly directed to the provision of a method of reducing the formation of scar tissue following laser irradiation of the cornea. The use of ultraviolet lasers, excimer lasers, Yag lasers and other types of lasers to alter the curvature of the cornea is a rapidly developing area of research in the field of ophthalmology. Such procedures include photorefractive keratectomy ("PRK") and phototherapeutic keratectomy ("PTK"). All such procedures are directed to altering the refractive properties of the cornea, and thereby correcting or at least improving the vision of patients afflicted with myopia, hyperopia and/or astigmatism. These procedures are collectively referred to herein as "refractive surgeries". The following textbook, and references cited therein, may be consulted for further details concerning such refractive surgeries: *Color Atlas/Text of Excimer Laser Surgery: The Cornea*, edited by Frank B. Thompson, M.D. and Peter J. McConnell, M.D., IGAKU-SHOIN Medical Publishers, Inc., New York, N.Y. (1993).

The advances in refractive surgeries over the past few years have been quite remarkable. However, clinical studies conducted to evaluate these procedures have shown that the procedures sometimes produce a phenomenon known as "corneal haze". Although this phenomenon is not yet fully understood, it is believed to involve an inflammatory response associated with healing of the ophthalmic tissues affected by the procedures, particularly the corneal epithelium and the stroma. The above-described methods are particularly useful to suppress or alter this inflammatory response associated with refractive surgeries. The above-described methods are also applicable to other forms of trauma to the cornea, such as surgical incisions. The methods may, for example, be employed in conjunction with incisions made in the cornea to correct vision, such as the procedure currently referred to as radial keratotomy, or in conjunction with the implantation of devices in the cornea to correct vision; one such device is known as the Intrastromal Corneal Ring.

What is claimed is:

1. A method of reducing the formation of scar tissue following trauma to the cornea, which comprises applying to the cornea at the site of the trauma a composition comprising: 0.001 to 10.000 ng/ml of TGF-$\beta_3$; and a pharmaceutically acceptable vehicle therefor.

2. A method according to claim 1, wherein the trauma resulted from an ophthalmic surgical procedure, and the composition is topically applied to the site of the trauma in conjunction with said procedure.

3. A method according to the claim 2, wherein the surgical procedure comprises a refractive surgery.

4. A method according to claim 3, wherein the refractive surgery comprises laser irradiation of the cornea.

5. A method according to claim 4, wherein the refractive surgery comprises irradiation of at least a portion of the corneal epithelium.

6. A method according to claim 4, wherein the refractive surgery comprises debridement of the corneal epithelium, followed by irradiation of the stroma.

7. A method according to claim 1, wherein the TGF-$\beta_3$ is human derived.

* * * * *